US00PP08376P

United States Patent [19]

Zaiger et al.

[11] Patent Number: Plant 8,376

[45] Date of Patent: Sep. 14, 1993

[54] PEACH TREE "STANISLAUS"

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 4005 California Ave., all of Modesto, Calif. 95351

[21] Appl. No.: 994,636

[22] Filed: Dec. 21, 1992

[51] Int. Cl.[5] ..... A01H 5/00

[52] U.S. Cl. ..... Plt./43.1

[58] Field of Search ..... Plt./43.1

*Primary Examiner*—James R. Feyrer

[57] ABSTRACT

A new and distinct variety of peach tree with the following unique combination of outstanding features that are desirable in a new variety.

1. Heavy and regular production of fruit.
2. Fruit that maintains an excellent shape, texture and appearance after being canned.
3. Very firm non-melting flesh suitable for mechanical pitters for stone removal.
4. Fruit with good flavor and eating quality both fresh and canned.
5. Vigorous semi-upright growth.
6. Relatively uniform maturity of firm fruit throughout the tree.
7. Fruit with good storage and shipping quality.

1 Drawing Sheet

ORIGIN OF THE VARIETY

The new present new variety of peach tree was originated by us in our experimental orchard located near Modesto, Calif. as a cross between Carolyn Peach (non-patented) and Loadel Peach (non-patented). A large group of these first generation seedlings were planted and grown under careful observation by use, during which time we recognized its distinct and desirable tree and fruit characteristics described above and selected the variety for reproduction and commercialization.

ASEXUAL REPRODUCTION OF THE VARIETY

Asexual reproduction of the new and distinct variety of peach tree was performed by budding in our experimental orchard located near Modesto, Calif. and shows that all characteristics run true to the original tree and are established and transmitted through succeeding propagations.

SUMMARY OF THE VARIETY

The new and distinct variety of peach tree is of large size, vigorous, semi-upright in growth and a regular and productive bearer of large, non-melting, yellow flesh clingstone fruit. The fruit is further characterized by having very firm flesh, ripening relatively uniform throughout the tree, having good handling and shipping quality, and maintaining an excellent shape, texture and appearance after being canned. In comparison to its pollen parent Loadel Peach (non-patented), the tree is more vigorous, has heavier production, larger size fruit, firmer non-melting flesh and is 7 to 8 days later in maturity.

PHOTOGRAPHS OF THE VARIETY

The accompanying photographic illustrations show typical specimens of the foliage and fruit of our new and distinct peach variety. The upper and lower surface of the leaves being illustrated with an exterior and sectional view of the fruit being displayed with the stone remaining in place. The illustrations were taken shortly after being picked at maturity (firm ripe) and the colors are as nearly true as reasonably possible in a color representation of this type.

DESCRIPTION OF THE VARIETY

The following is a detailed botanical description of the new and distinct variety of peach tree, its flowers, foliage and fruit, as based on observations of specimens grown in our experimental orchard located near Modesto, Calif., with color terminology (except those in common terms) in accordance with Reinhold Color Atlas by A. Kornerup and J. H. Wanscher.

Tree:

*Size.*—Large.

*Vigor.*—Vigorous.

*Form.*—Semi-upright, normally pruned to vase shape.

*Production.*—Productive.

*Bearer.*—Regular.

*Density.*—Medium dense.

Trunk:

*Size.*—Medium to stocky.

*Texture.*—Medium shaggy.

*color.*—Grayish brown to brown (6-E-3) to (6-E-5).

Branches:

*Size.*—Medium.

*Texture.*—Medium rough.

*Lenticels.*—Medium number. Medium to large size.

*Color.*—Brown to dull brown.

Leaves:

*Size.*—Large. Average length — 6¼". Average width — 1½".

*Form.*—Lanceolate. Acutely pointed.

*Texture.*—Smooth.

*Margin.*—Crenate.

*Petiole.*—Medium length. Medium thickness.

*Gland.*—Globose. Medium size. Number varies from 1 to 3. Average number 2. Positioned on upper portion of petiole and at the base of the leaf blade, usually alternate.

*Color.*—Upper surface — green to dark green (27-F-4) to (27-F-8). Lower surface — grayish green to green (26-E-4) to (26-E-6).

Flower buds:

*Size.*—Medium.

*Form.*—Plump.

*Pubescence.*—Pubescent.

Flowers:

*Size.*—Small — non-showy.

*Blooming period.*—Mar. 1, 1992 to Mar. 8, 1992. Varies slightly with climatic conditions.

*Pollen.*—Present.

*Color.*—Pink — fades to light pink at petal fall.

Fruit:

*Maturity when described.*—Firm ripe.

*Date of first picking.*—Jul. 10, 1992.

*Date of last picking.*—Jul. 14, 1992.

*Size.*—Large. Average diameter axially — $2\frac{7}{8}''$ to $3\frac{1}{8}''$. Average transversely in suture plane — $2\frac{7}{8}''$ to $3\frac{1}{8}$.

*Suture.*—Shallows, distinct, extends from base to apex.

*Ventral surface.*—Slightly lipped at suture line.

*Form.*—Nearly globose, slightly flattened at stem end.

*Base.*—Retuse.

*Cavity.*—Rounded, slightly elongated in suture plane. Average depth — $\frac{5}{8}''$. Average breath — $1''$.

*Apex.*—Usually rounded, varies from slight pistil point to slight depression.

Flesh:

*Texture.*—Very firm, non-melting.

*Ripens.*—Even.

*Juice.*—Light to moderate.

*Flavor.*—good.

*Eating quality.*—Good.

*Aroma.*—Light.

*Color.*—Yellow to butter yellow — (3-A-6) to (4-A-5).

Skin:

*Thickness.*—Medium.

*Texture.*—Medium.

*Tendency to crack.*—None.

*Down.*—Moderate.

*Color.*—Light yellow ground color — (3-A-5) to (4-A-4) very slight red blush (9-A-5) to (9-A-6).

Stone:

*Type.*—Clingstone.

*Size.*—Large. Average length — $1\frac{1}{2}'$. Average breadth — $1\frac{1}{4}''$. Average thickness — $\frac{5}{8}''$.

*Form.*—Oval.

*Base.*—Varies from round to straight.

*Apex.*—Varies from round to slight point.

*Surface.*—Irregularly furrowed toward apex, pitted toward base.

*Tendency to split.*—Very slight.

*Color.*—Light brown to reddish brown (8-D-7) to (9-D-7).

Use: Canned.

Keeping quality: Good.

Shipping quality: Good.

pg,7

The new and distinct peach tree, its flowers, foliage and fruit herein described may vary in slight detail due to climatic, soil conditions and cultural practices under which the variety may be grown, the present description is that of the variety grown under the ecological conditions prevailing near Modesto, Calif.

We claim:

1. A new and distinct variety of peach tree, substantially as illustrated and described, characterized by its large size, vigorous, semi-upright growth and a regular and productive bearer of large, non-melting, very firm, yellow flesh clingstone fruit which after being canned maintains an excellent shape, texture and appearance with good flavor and eating quality; the tree is further characterized in comparison to the Loadel peach (non-patented) by being more vigorous, larger in size and producing larger, firmer fruit which are approximately 7 to 8 days later in maturity.

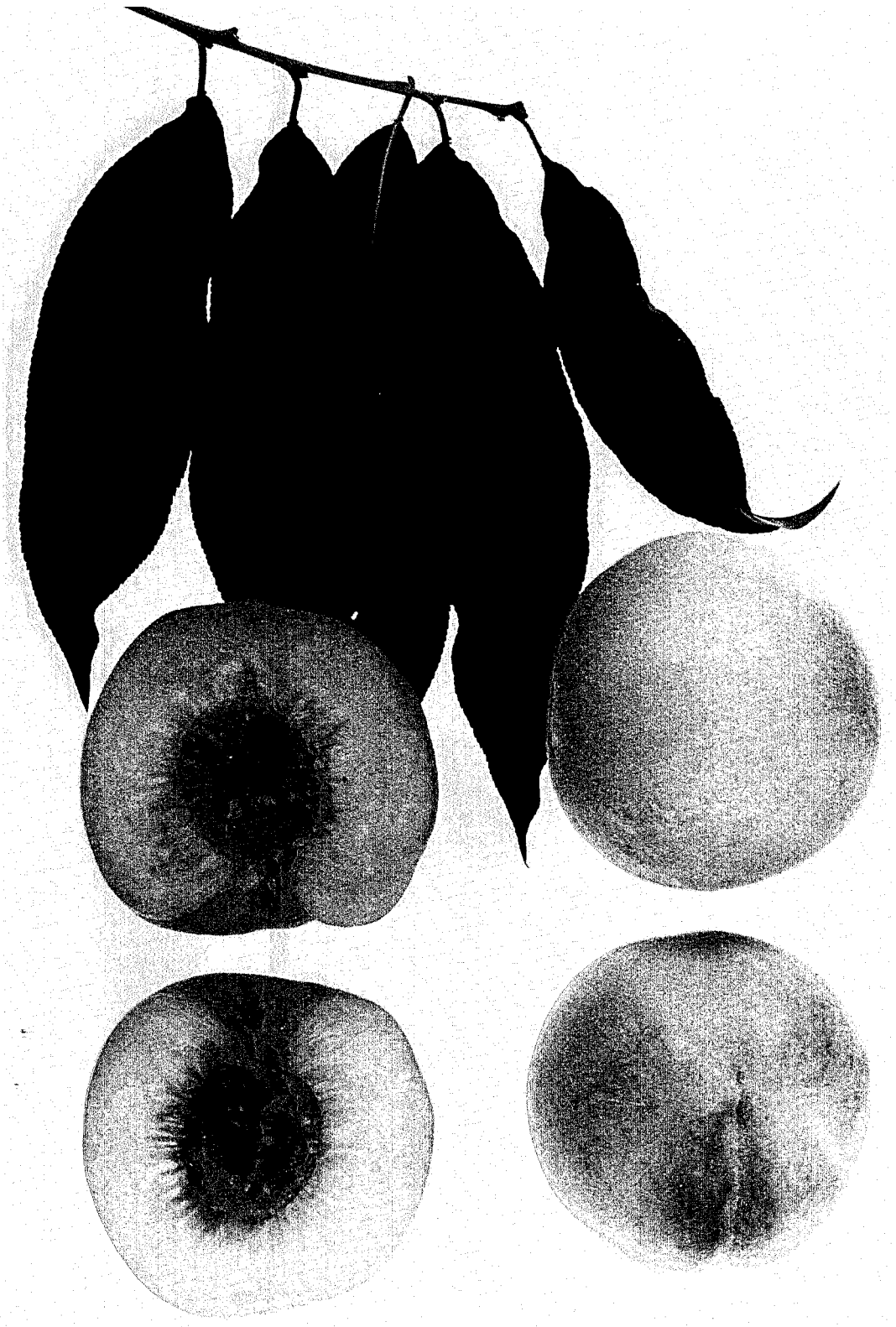

* * * * *